United States Patent [19]

Brush et al.

[11] 4,254,140
[45] Mar. 3, 1981

[54] 4-(2-AMINOETHYL)-7-HYDROXY-2-METHYL-2,3-DIHYDROBENZOFURANS

[75] Inventors: Charles K. Brush, Malvern; Joseph Weinstock, Phoenixville, both of Pa.

[73] Assignee: SmithKline Corporation, Philadelphia, Pa.

[21] Appl. No.: 132,041

[22] Filed: Mar. 20, 1980

[51] Int. Cl.³ .................... A61K 31/34; C07D 307/86
[52] U.S. Cl. ............................... 424/285; 260/346.73
[58] Field of Search ................... 260/346.73; 424/285

[56] References Cited

FOREIGN PATENT DOCUMENTS 1384843  2/1975  United Kingdom .

Primary Examiner—Henry R. Jiles
Assistant Examiner—Bernard Dentz
Attorney, Agent, or Firm—William H. Edgerton; Richard D. Foggio; Alan D. Lourie

[57] ABSTRACT 4-(2-Aminoethyl)-7-hydroxy-2-methyl-2,3-dihydrobenzofuran derivatives having dopaminergic activity are prepared by cyclizing a 2-allyl-3,4-dimethoxyphenethylamine such as by reacting the phenethylamine with hydrogen bromide.

8 Claims, No Drawings

4-(2-AMINOETHYL)-7-HYDROXY-2-METHYL-2,3-DIHYDROBENZOFURANS

This invention comprises a group of new chemical compounds whose structures have a 2,3-dihydrobenzofuran nucleus characterized by having an aminoalkyl substituent at position 4 and a hydroxy substituent at position 7. The compounds have dopaminergic activity especially at peripheral receptor sites as demonstrated by a renal vasodilator effect.

DESCRIPTION OF THE PRIOR ART

A number of 2,3-dihydrobenzofuran compounds have been described to have biological activity. Most of these have carboxy or a β-blocking group (i.e. 2-tert.-butylamino-1-hydroxypropyl) substituted on the nucleus. French Pat. No. 2,244,458 discloses 2-alkyl-2,3-dihydrobenzofuran compounds whose structures are substituted with an α-aminoethyl group at 5 and a chloro group at 7 which compounds have antiinflammatory activity. None of the references known to the applicants describe the characteristic structural features or the dopaminergic activity of the compounds of the present invention.

DESCRIPTION OF THE INVENTION

The compounds of this invention are represented by the following structural formula:

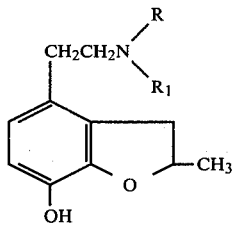

I in which R and $R_1$ are hydrogen or lower alkyl of 1-6 carbons preferably both are propyl.

The pharmaceutically acceptable acid addition salts having the utility of the free bases of Formula I, prepared by methods well known to the art, are formed with both inorganic or organic acids, for example: maleic, fumaric, benzoic, ascorbic, pamoic, succinic, bismethylenesalicylic, methane sulfonic, ethane disulfonic, acetic, oxalic, propionic, tartaric, salicylic, citric, gluconic, aspartic, stearic, palmitic, itaconic, glycolic, p-aminobenzoic, glutamic, benzene sulfonic, hydrochloric, hydrobromic, sulfuric, cyclohexylsulfamic, phosphoric and nitric acids. The hydrohalic and especially methane sulfonic acid salts are of particular utility.

The compounds of Formula I are prepared by the following reaction:

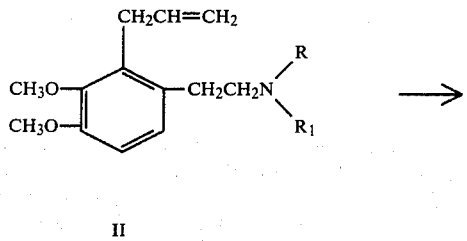

II

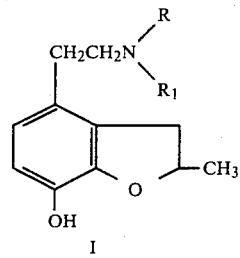

I in which R and $R_1$ are as described above.

The cyclization reaction (II→I) is most conveniently carried out by reacting hydrogen bromide in a suitable solvent such as glacial acetic acid with a 2-allyl-3,4-dimethoxyphenethylamine (II) usually at reflux until the reaction is complete. The reaction time and temperature may be varied from several days at room temperature to ½ or 1 hour at reflux temperature. Hydriodic acid or 48% hydrobromic acid are also alternatives. When the reaction is carried out using a hydrohalic acid, the methyl ether at 7 is split as well to give the desired compounds of this invention.

Alternative cyclization agents known to the art may be used as well, for example, trifluoroacetic acid-sulfuric acid, sulfuric acid, polyphosphoric acid or methane sulfonic acid in methylene chloride as well as known Lewis acid cyclizing agents such as boron trifluoride, aluminum chloride or stannic chloride. In using certain of these one may obtain as a product of the cyclization reaction the 7-methoxy substituted compound which methoxy group is then split using boron tribromide or hydrogen bromide to give the desired compound. In the preferred aspect of this reaction which uses a hydrohalide cyclizing agent such as 30% hydrogen bromide in glacial acetic acid good yields of the desired 4-(2-aminoethyl)-7-hydroxy-2-methyl-2,3-dihydrobenzofuran are obtained in a simple one-step reaction.

The compounds of this invention have been demonstrated to have peripheral dopaminergic activity as measured by monitoring mean arterial blood pressure (MAP), mean renal blood flow (RBF), renal vascular resistance (RVR) and heart rate (HR) in the normal anesthetized dog. As examples of the activity in this pharmacological procedure the following results were obtained for 7-hydroxy-2-methyl-4-(2-di-n-propylaminoethyl)-2,3-dihydrobenzofuran hydrobromide (A) and 4-(2-aminoethyl)-7-hydroxy-2-methyl-2,3-dihydrobenzofuran hydrobromide (B).

| Compound | Dose μg/Kg/min | % Change MAP | RBF | RVR | HR |
|---|---|---|---|---|---|
| Dopamine | 3 | +6.1 | +28.0* | −26.0* | −1.4 |
| A | 3 | −2.7 | +2.0 | −4.6 | 0 |
|  | 30 | +0.4 | +14.5* | −12.2* | +1.6 |
|  | 300 | −0.6 | +9.0* | −8.7 | +1.5 |
| Dopamine | 3 | −3.7 | +40.6* | −31.5* | −3.7 |
| B | 3 | −1.5 | +7.9* | −8.8 | −1.3 |
|  | 30 | +0.3 | +9.9* | −8.4 | +2.4 |
|  | 300 | −0.6 | +13.6* | −12.9* | 0 |

*Significant for two dogs.

In the secondary testing in the anesthetized dog administration of Compound A intravenously to three dogs at infusion rates from 0.1 to 810 μg/kg/min gave an $ED_{15}$ of 30.0 μg/kg., dopamine 3.5 μg/kg. Compound A gave no positive results as a diuretic in the phosphate-mannitol renal clearance procedure in the unanesthetized dog. Compound B at 20 mg/kg orally showed a significant increase in $K \oplus$ and $Cl \oplus$ excretion. Neither did it demonstrate activity in the rotation test in lesioned rats for central dopaminergic activity. Therefore, the compounds possess a non-specific peripheral dopaminergic activity. As such they are of use in treating cardiovascular disorders such as hypertension or other clinical symptoms which are treated with dopamine.

The pharmaceutical compositions of this invention having peripheral dopaminergic activity are prepared in conventional dosage unit forms by incorporating a compound of Formula I, or a pharmaceutically acceptable acid addition salt or ester derivative thereof, with a nontoxic pharmaceutical carrier according to accepted procedures in a nontoxic amount sufficient to produce the desired pharmacodynamic activity in a subject, animal or human. Preferably the compositions will contain the active ingredient in an active but nontoxic amount selected from about 50 mg to about 500 mg preferably about 75-250 mg of active ingredient per dosage unit but this quantity depends on the relative potency of the basic compound compared with dopamine, the specific biological activity desired, the route of administration whether oral or parenteral, and the condition of the patient.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are isotonic saline for parenteral use or syrup, peanut oil, olive oil, water and the like for soft gelatin capsules. Similarly the carrier or diluent may include any time delay material well known to the art, such as glyceryl monostearate or glyceryl distearate alone or with a wax. Such sustained release products as well as derivatives which may be gradually metabolized to the active parent can be employed to prolong the unique biological activity of the compounds of this invention.

A wide variety of pharmaceutical forms can be employed. Thus, if a solid carrier for oral administration is used the preparation can be tableted, placed in a hard gelatin capsule in powder, regular or sustained release pellet form, or in the form of a troche or lozenge. the amount of solid carrier will vary widely but preferably will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing peripheral dopaminergic activity in accordance with this invention comprises administering orally or parenterally to a subject in need of such activity a compound of Formula I or a pharmaceutically acceptable acid addition salt thereof, usually combined with a pharmaceutical carrier, in a nontoxic amount sufficient to produce said activity as described above. The route of administration may be any route which effectively transports the active compound to the peripheral dopamine receptors which are to be stimulated such as orally or parenterally, the oral route being preferred. The parenteral administration may be subcutaneous or intravenous. Advantageously, equal oral doses within the ranges given above will be administered several times, such as from one to five times a day, with the daily dosage regimen being selected from about 50 mg to about 1.0 g, preferably 75–500 mg, for oral dosage units. When the method described above is carried out dopaminergic activity is produced. For an average size human for the preferred species (A) a preferred oral dose to show anti-hypertensive activity would be selected from the range of from about 100–250 mg of base for each dosage unit adapted for oral administration to be administered from 1–5 times daily.

The following examples are designed solely to illustrate the preparation and use of the compounds of this invention. The temperatures are Centigrade. Other variations of these examples will be obvious to those skilled in the art.

EXAMPLE 1

A mixture of 41.4 g. (0.183 mole) of 2-allyl-3,4-dimethoxybenzyl chloride [R. Schwarz et al., Monatsh. 84 595 (1953)] and 210 ml of dimethylformamide was mixed with 10.5 g (0.214 mole) of sodium cyanide. The mixture was heated at 60° for 1.5 hours. Water (100 ml) was added until the solid present dissolved. The reaction mixture was then poured into 1 l. of water. The diluted reaction mixture was extracted twice with ether. The ether extract was backwashed with water, dried and evaporated to give 37.9 g. (75.6%) of oily 2-allyl-3,4-dimethoxyphenylacetonitrile. Nuclear magnetic resonance spectrum (NMR) checked.

The acetonitrile (15.25 g., 0.07 mole) in 100 ml of dry tetrahydrofuran was added dropwise over 20 minutes to a previously prepared solution of 3.15 g. (0.105 mole) of aluminum hydride in 140 ml. of dry tetrahydrofuran under argon. After stirring for 1.25 hours at ambient temperature, the mixture was worked up by adding sequentially 3.8 ml. of water, 3.8 ml. of 10% sodium hydroxide and 10 ml. of water. After separating the solid, the filtrate was evaporated to give 2-allyl-3,4-dimethoxy-$\beta$-phenethylamine as an oil. NMR checked.

The phenethylamine (9.5 g., 0.037 mole) was dissolved in 40 ml of 30% hydrogen bromide in acetic acid. After heating at reflux for ¾ hour, an additional 10 ml. of hydrogen bromide:acetic acid was added followed by a ½ hour reflux period. The cooled reaction mixture was allowed to stand over the weekend to crystallize; 7.2 g. (71%) of 7-hydroxy-2-methyl-4-(2-aminoethyl)-2,3-dihydrobenzofuran hydrobromide. A sample was recrystallized from ethanol m.p. 211°–214°. $C_{11}H_{15}NO_2 \cdot HBr$ Anal. Calcd: C, 48.34; H, 6.01; N, 5.35; Found: C, 48.19; H, 5.88; N, 5.11

A sample of the base (750 mg.) in tetrahydrofuran was prepared by shaking the salt in tetrahydrofuran-sodium carbonate solution. One aliquot was evaporated to give the free base, another was reacted with methane sulfonic acid to give the methane sulfonic acid salt.

EXAMPLE 2

A mixture of 20.9 g. (0.096 mole) of 2-allyl-3,4-dimethoxyphenylacetonitrile, 120 ml. of 40% sodium hydroxide solution and 200 ml. of ethanol was heated at reflux for 2 hours. The cooled mixture was extracted with ether. The basic solution was neutralized and the separated solid taken into ether. The dried ether extract was evaporated to leave 18.7 g. (82%) of an oily 2-allyl-3,4-dimethoxyphenylacetic acid. NMR checked for named structure and absence of propenyl benzene derivatives.

The phenylacetic acid (11 g., 0.0466 mole) was dissolved in 165 ml. of methylene chloride. After 20 ml. of thionyl chloride was added, the reaction mixture was heated at reflux for 1½ hours. The mixture was stripped. The residue was taken up in methylene chloride and 3 equivalents of di-n-propylamine were added dropwise. After ½ hour, the solution was extracted with dilute hydrochloric acid, sodium bicarbonate solution then dried and evaporated to give 14.3 g. (96%) of oily 2-allyl-3,4-dimethoxy-N,N-dipropylphenylacetamide. NMR checked.

A mixture of 2.13 g. of lithium aluminum hydride in 200 ml. of dry ether was swept with argon then a mixture of 14.3 g. (0.045 mole) of the N,N-dipropylacetamide in dry ether was added dropwise. The reaction mixture was heated at reflux for 4 hours. The mixture was quenched by careful addition of 0.5 ml. of water, 0.5 ml. of 10% sodium hydroxide solution and then 6.5 ml. of water. The precipitate was separated and washed with ethyl acetate. The filtrate was acidified with ethanolic hydrogen chloride then stripped. The residue was recrystallized from ethyl acetate:ether to give 10.9 g. (71%) of N,N-dipropyl-2-allyl-3,4-dimethoxyphenethylamine. The material was recrystallized from ethyl acetate, m.p. 116°–117.5° as the hydrochloride.
$C_{19}H_{31}NO_2.HCL.\frac{1}{4}H_2O$ Anal. Calcd: C, 65.88; H, 9.46; N, 4.04; Found C, 66.24; H, 9.49; N, 3.98

A mixture of 3.57 g. of the N,N-dipropylphenethylamine in 25 ml. of 30% hydrogen bromide in acetic acid was stirred for 4 days, then heated at 100° for 3 hours. After standing overnight at room temperature, the acetic acid was evaporated in vacuo. The residue was dissolved in methanol. The methanol was stripped off. The residue was redissolved in hot methanol and crystallized by adding ethyl acetate to give 1.8 g. (43%) of 7-hydroxy-2-methyl-4-(2-di-n-propylaminoethyl)-2,3-dihydrobenzofuran hydrobromide. A sample was dissolved in hot methanol, treated with activated charcoal and recrystallized from methanol:ethyl acetate, m.p. 166°–168°.
$C_{17}H_{27}NO_2.HBr$ Anal. Calcd: C, 56.98; H, 7.68; N, 3.91; Found: C, 56.81; H, 7.65; N, 3.96

The free base is obtained by shaking the hydrobromide (500 mg.) in a mixture of ether-sodium carbonate solution, separating the ether layer and evaporating the dried solvent.

Substituting dimethylamine or tert.-butylamine for the dipropylamine in the above reactions gives 7-hydroxy-4-(2-dimethylaminoethyl)-2-methyl-2,3-dihydrobenzofuran as the hydrochloride and 7-hydroxy-4-(2-tert.-butylaminoethyl)-2-methyl-2,3-dihydrobenzofuran as the base as well as the hydrobromide.

EXAMPLE 3

| Ingredients | Mg. per Capsule |
| --- | --- |
| 7-Hydroxy-2-methyl-4-(2-di-n-propylaminoethyl)-3,4-dihydrobenzofuran hydrobromide | 150 (base) |
| Magnesium stearate | 2 |
| Lactose | 200 |

The ingredients are thoroughly mixed and filled into a hard gelatin capsule. One capsule is administered orally to patients in need of peripheral dopaminergic activity from 1–5 times daily.

What is claimed is:

1. A compound of the structural formula:

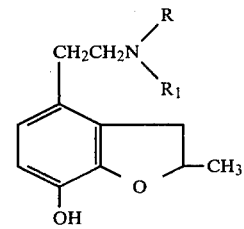

in which R and $R_1$ are hydrogen or lower alkyl of 1–6 carbons; together with pharmaceutically acceptable acid addition salts thereof.

2. The compound of claim 1 in which R and $R_1$ are both n-propyl or both hydrogen.

3. The compound of claim 1 being 7-hydroxy-4-(2-di-n-propylaminoethyl)-2-methyl-2,3-dihydrobenzofuran.

4. The compound of claim 1 being 7-hydroxy-4-(2-di-n-propylaminoethyl)-2-methyl-2,3-dihydrobenzofuran hydrobromide.

5. The compound of claim 1 being 7-hydroxy-4-(2-aminoethyl)-2-methyl-2,3-dihydrobenzofuran hydrobromide.

6. The compound of claim 1 being 7-hydroxy-4-(2-aminoethyl)-2-methyl-2,3-dihydrobenzofuran.

7. The method of inducing peripheral dopaminergic activity in a subject in need thereof comprising administering orally or parenterally to said subject a compound of claims 1, 2, 3, 4, 5 or 6.

8. A pharmaceutical composition having peripheral dopaminergic activity comprising a nontoxic dopaminergic quantity of a compound of claims 1, 2, 3, 4, 5 or 6 combined with a pharmaceutical carrier.

* * * * *